US006162434A

United States Patent [19]

Buelow

[11] Patent Number: 6,162,434

[45] Date of Patent: Dec. 19, 2000

[54] CYTOMODULATING PEPTIDE FOR INHIBITING LYMPHOCYTE ACTIVITY

[75] Inventor: Roland Buelow, Palo Alto, Calif.

[73] Assignee: Sangstat Medical Corporation, Fremony, Calif.

[21] Appl. No.: 08/433,613

[22] Filed: May 3, 1995

[51] Int. Cl.[7] .......................... A61K 38/04; A61K 38/08; A61K 38/17; C07K 7/00

[52] U.S. Cl. .................................... 424/185.1; 424/184.1; 514/2; 514/13; 514/885; 530/300; 530/326; 530/350; 530/403; 530/868; 530/329

[58] Field of Search .............................. 424/184.1, 185.1; 514/2, 13; 530/300, 326, 350, 403, 868, 329; 574/885

[56] References Cited

FOREIGN PATENT DOCUMENTS

| | | |
|---|---|---|
| WO88/05784 | 8/1988 | WIPO . |
| WO93/08817 | 5/1993 | WIPO . |
| WO 93/17699 | 9/1993 | WIPO . |
| WO 94/02162 | 2/1994 | WIPO . |
| WO95/13288 | 5/1995 | WIPO . |

OTHER PUBLICATIONS

Buelow et al., Immunomodulation by Soluble HLA Class I (1995) *Transplantation*, vol. 59, No. 5:649–654.

Wood, W. B. et al. (Eds.) Biochemistry Benjamin/Cummings Publishing Co., Menlo Park, CA, pp. 14–15, 1981.

Bjorkman, P. J. et al. Nature 329: 506–512 (1987) Mar. 21, 2000.

Dal Porto, J. et al. Proc. Natl. Acad. Sci. USA 90: 6671–6675 (1993).

*Primary Examiner*—Phillip Gambel
*Attorney, Agent, or Firm*—Flehr Hohbach Test Albritton & Herbert LLP

[57] ABSTRACT

Novel oligopeptides comprising a sequence associated with HLA-B $\alpha_1$ domain, but comprising a tyrosine-tyrosine-tryptophan triad are provided for use in inhibiting cytotoxic activity of CTLs and natural killer cells. By combining the subject compositions with mixtures of cells comprising the cytotoxic cells and cells which would otherwise activate the cytotoxic cells, lysis of the target cells can be substantially inhibited. The oligopeptides may be joined to a wide variety of other groups or compounds for varying the activity of the subject compositions. The subject compositions may be administered by any convenient means to a host to inhibit CTL and NK attack on tissue, particularly involved with xenogeneic or allogeneic transplants.

12 Claims, No Drawings

CYTOMODULATING PEPTIDE FOR INHIBITING LYMPHOCYTE ACTIVITY

TECHNICAL FIELD

The field of this invention is the modulation of T cell activity.

BACKGROUND

The immune system is an extraordinarily complex combination of cells and compositions to protect a mammalian host against a wide variety of pathogens, while surveiling the body against aberrations, such as neoplasia. One branch of the immune system involves T cells, which derive their designation by the fact that they are processed by the thymus. The T cells are a complex group of cells which differ as to markers such as CD3, CD4 and CD8, as well as other markers which indicate whether the T cells are in the quiescent or activated state, the homing receptors, which determine the tissue to which T cells will be directed and extravasate, as well as the nature of the targets for the T cells. The T cells may be cytotoxic, having numerous mechanisms for inducing cell death, or activating, by secreting various cytokines which activate other cells.

Among the various subsets of T cells are T cells referred to as cytotoxic T lymphocytes ("CTL"). The CTLs act by being restricted to a particular major histocompatibility complex antigen complex. The CTLs carry a receptor called the T cell receptor, which comprises an $\alpha$ chain and a $\beta$ chain, with the two chains being polymorphic. The $\alpha$ and $\beta$ chains of the T cell receptor have specific affinity for a particular MHC complex associated with a peptide in the groove of the MHC. The CTLs have been screened so that the CTLs do not act against cells where the peptide in the groove is endogenous to the host. Where the MHC is foreign or the peptide in the groove is foreign to the host, the CTLs will attack such cells and kill them. There are a variety of pathways by which CTLs may kill target cells.

Other lymphocytic cells involved in the immune system include Natural Killer (NK) cells, which do not carry the markers normally associated with B and T lymphocytes. As distinct from CTL cells, the NK cells have a more random repetoire than the CTL cells. The NK cells appear to lyse certain tumor cells and cells lacking expression of certain MHC proteins, but do not normally lyse normal cells. The NK cells, in common with CTL cells, express a surface ganglioside called asialo GM-1, CD2, and CD16

While the monitoring function is extremely important to a host's health, there are a number of situations where activation of CTLs is undesired. One particular area is associated with transplantation, where one rarely has an identical match between the donor and recipient of the MHC antigens. Another incidence is where there is a failure on the part of the CTLs in that they attack cells where the peptide and MHC are both endogenous, as occurs in autoimmune diseases.

Immunosuppression has become a general approach in situations where activation of CTLs is undesired. However, immunosuppressants such as cyclosporin A, FK506, and the like, have numerous side effects which are undesirable. There is, therefore, substantial interest in identifying new agents which can act to inhibit the activation of CTLs while having less of a universal effect on the immune system and fewer side effects, so as to leave the host with a substantial proportion of the immune system for protection against adventitious infection.

Relevant Literature

Buelow et al., Transplantation (1995) 59:649–654 and references cited therein.

SUMMARY OF THE INVENTION

CTL and NK cell cytomodulating peptides are provided having the tripeptide tyrosine-tyrosine-tryptophan, where the N terminus is extended by at least 3 amino acids, of the human Class I HLA-B $\alpha_1$-domain, having from 0 to 2 mutations, usually of non-conserved amino acids, dimers thereof and D-stereoisomers thereof. The peptides find use in inhibiting activation or cytotoxic lymphocytes, either by themselves of in conjunction with other immunosuppressing agents. Administration may be ex vivo of an organ to be transplanted or in vivo by any convenient means, in sufficient amount to substantially inhibit lymphocytic activation.

DESCRIPTION OF THE SPECIFIC EMBODIMENTS

Methods and compositions are provided for modulating lymphocytic activity, particularly CTL and NK cell activity, in vitro and in vivo. The compositions comprise oligopeptides of at least 6 amino acids comprising the tripeptide or triad (SEQ ID NO: 1) TYR-TYR-TRP (YYW), preferably the tetrapeptide (SEQ ID NO: 2) ARG-TRY-TYR-TRP (RYYW).

At the N terminus of the tripeptide or triad, there will usually be at least about 4 amino acids, more usually at least about 5 amino acids, where for the most part, these amino acids will be determined by amino acids from Class I HLA-B $\alpha_1$-domain amino acids 80 to 83, more usually 78 to 83, frequently 75 to 83, or the equivalent thereof of other species, e.g. mouse, rat, etc., and may be extended even further, although as the oligopeptide is extended, an increasing number of substitutions from the natural sequences are permissible.

The C terminus of the triad may also be extended, usually by not more than 5 amino acids, more usually by not more than 3 amino acids, frequently not more than 1 amino acid.

Also included are dimers of the oligopeptides, which may be head to head, tail to tail, or head to tail. In addition, 1 or more of the amino acids may be the D-stereoisomer, up to all of the amino acids.

Also, structurally constrained oligopeptides may be employed, such as cyclic peptides of from about 8 to 50, usually 12 to 36 amino acids, where amino acids other than the specified amino acids may be present as a bridge. In some instances, one may use other than amino acid bridges. By having terminal cysteines, one may form a disulfide bridge to close the ring. Alternative methods for ring formation may be found in Chen et al., P.N.A.S. USA (1992) 89:5872–5876; and Wu et al., Protein Engineering (1993) 6:471–478.

For the most part, the oligopeptides will have at least 6, usually at least 8, amino acids, include the triad and come within the following formula: $aa^{70}$ $aa^{71}$ Q $aa^{73}$ $aa^{74}$ R $aa^{76}$ $aa^{77}$ L $aa^{79}$ $aa^{80}$ $aa^{81}$ $aa^{82}$ $aa^{83}$ Y Y W $aa^{87}$ $aa^{88}$ $aa^{89}$ $aa^{90}$ $aa^{91}$ (SEQ ID NO: 56).

Wherein:

$aa^{70}$ is Q, H, S, N or K, particularly Q or H;

$aa^{71}$ is an aliphatic neutral amino acid, including S, A and T, particularly S;

$aa^{73}$ is T or A;

$aa^{74}$ is Y or H;

$aa^{76}$ is an aliphatic neutral amino acid, particularly V;

$aa^{77}$ is S or N;

$aa^{79}$ is R or G, particularly G;

$aa^{80}$ is T, I, N or an aromatic amino acid, e.g., F, W or Y, particularly T or I;

$aa^{81}$ is an aliphatic non-polar amino acid including L or A, particularly A;

$aa^{82}$ is R, L or an aromatic amino acid, particularly L;

$aa^{83}$ is G or R, particularly R;

$aa^{87}$ is any amino acid, particularly neutral aliphatic or aromatic, G, A, S, T, M, N, Q, F, W, or Y, more particularly, A, W, F, N, Q, or S;

$aa^{88}$ is an aromatic amino acid or aliphatic amino acid of from 5 to 6 carbon atoms, particularly F, W, Y, L, I or V;

$aa^{89}$ is is any amino acid, particularly neutral aliphatic or aromatic, G, A, S, T, M, N, Q, F, W, or Y, more particularly, A, W, F, N, Q, or S;

$aa^{90}$ is any amino acid, particularly neutral aliphatic or aromatic, G, A, S, T, M, N, Q, F, W, or Y, more particularly, A, W, F, N, Q, or S; and $aa^{91}$ is any amino acid, particularly neutral aliphatic or aromatic, G, A, S, T, M, N, Q, F, W, or Y, more particularly, A, W, F, N, Q, or S.

Desirably for amino acids after $aa^{86}$ (W), the amino acids will alternate with an aromatic amino acid separated by an aliphatic amino acid, particularly a neutral aliphatic amino acid.

For the most part, the peptides will be at least 6 amino acids, more usually at least 8 amino acids, frequently at least 10 amino acids and up to the entire sequence of 22 amino acids or the dimer of 44 amino acids for the active sequence. The active sequence may be bonded or non-covalently linked within a chain or as a side chain of other peptides or proteins, for a variety of purposes.

Compositions of particular interest will have the following formula: (SEQ ID NO: 3)

RV/EN/DLRIA/LLR/EYYWQ/DS

Wherein: the backslashes intend that either amino acid may be present at that position. The preferred compositions will have at least 8 amino acids, preferably at least about 10 amino acids, where the 10 amino acids includes a sequence within the above formula which includes the tripeptide YYW. Desirably, the sequence terminates with W.

The subject sequences find use in a variety of ways. For research purposes, they may be used for analyzing the physiological pathway associated with activation and deactivation of CTLs. One can combine CTLs, particularly CTL cell lines having known peptide targets in conjunction with the subject peptides, particularly radioactively labeled, in the presence and absence of antigen presenting cells to which the CTLs are restricted. After the lysis by the CTLs, one may then separate the activated CTL cells from quiescent CTL cells by means of the marker CD69, which marker is upregulated in vitro upon activation. Separation can be achieved using a FACS and a fluorescent labeled anti-CD69.

By isolating the most fluorescent cells, e.g. the highest 25%, one then lyses the cells and isolates proteins associated with the subject markers, e.g. chromatography, non-denaturing electrophoresis, or the like. Alternatively, one separates the proteins using electrophoresis and then uses a Western blot or other technique with the labeled peptides to identify proteins with which the subject peptides bind. Instead of a radiolabel, any other type of label may be employed, normally a small organic molecule, such as biotin, a fluorescer, and the like. Where biotin is used, after separation, avidin may be added, where the avidin is labeled with a label as described previously.

One may also compare T cells which have been combined with antigen presenting cells in the presence and the absence of the subject peptides. cDNA libraries may be prepared in each instance and representational differential analysis, subtraction, or the like may be employed to detect the differences in expression between the cells which have been activated in the presence and the absence of the subject peptides. One may also determine whether particular subsets of CTLs respond differently from other subsets to the subject peptides by their expression or lack of expression or one or more proteins, particularly surface membrane proteins. In this way, CTLs may be identified which may be removed by leukophoresis or the like, in order to diminish an unwanted CTL attack on tissue.

It has been reported that peptides of the HLA-B $\alpha_1$ domain bind to Hsc70, which is known to serve as a chaperonin and bind to a variety of sequences in its role as chaperonin.

Depending upon their intended use, particularly for administration to mammalian hosts, the subject peptides may be modified widely to change their distribution in the blood stream, diminish or enhance binding to blood components, enhancing the lifetime of a peptide in the blood stream, and the like. The subject peptides may be bound to these other components by linkers which are cleavable or non-cleavable in the physiological environment of the blood. The peptides may be joined at any point of the peptide where a functional group is present, such as hydroxyl, thiol, carboxyl, amino, or the like. Desirably, binding will be at either the N-terminus or the C-terminus.

The peptide may be joined to a wide variety of other oligopeptides or proteins for a variety of purposes. For example, the subject peptides may be covalently linked to an immunogen to produce antibodies to the subject peptides, where the antibodies may serve for identification of other peptides having a comparable conformation. In addition, the antibodies may be used to prepare anti-idiotypic antibodies which may compete with the subject peptides for binding to a target site. These anti-idiotypic antibodies may then be used for identifying proteins to which the subject peptides bind. Alternatively, the subject peptides may be expressed in conjunction with other peptides or proteins, so as to be a portion of the chain, either internal, or at the N- or C-terminus. By providing for expression of the subject peptides, various post-expression modifications may be achieved. For example, by employing the appropriate coding sequences, one may provide for lipidation, e.g., prenylation or myristoylation. In this situation, the subject peptide will be bound to a lipid group at a terminus, so as to be able to be bound to a lipid membrane, such as a liposome. For administration, liposomes may be used, where drugs may be introduced into the lumen of the liposome, so as to cooperate with the subject peptides in diminishing CTL activation. Thus, immunosuppressants may be included in the lumen, so that the subject peptide and immunosuppressant may act in a localized manner.

The subject peptides may be PEGylated, where the polyethyleneoxy group provides for enhanced lifetime in the blood stream. The subject peptides may also be combined with other proteins, such as the Fc of an IgG isotype, which may be complement binding or not bind complement, or with a toxin, such as ricin, abrin, diphtheria toxin, or the like, particularly the A chain.

The subject peptides may be modified in a wide variety of ways. Sequence analogs may be prepared by oligopeptide synthesis using a stepwise substitution of the amino acids at each position with alanine or valine, particularly alanine. Generally the total number of amino acids substituted will not exceed 3, ranging from 1 to 3, usually 1 to 2. Methods of producing "scanning" mutations are known in the art, and have been successfully used with a number of different peptides. Examples of protocols for scanning mutations may be found in Gustin, et al. (1993) *Biotechniques* 14:22; Barany (1985) *Gene* 37:111–23; Colicelli, et al. (1985) *Mol Gen Genet* 199:537–9 and Prentki, et al. (1984) *Gene* 29:303–13.

One can prepare these compositions by preparing a gene coding for the particular peptide or protein, joined to a DNA sequence coding for the subject peptide. The gene may be introduced into an appropriate expression vector, there being many expression vectors commercially available, whereby the gene is then expressed in an appropriate host. See, Sambrook et al., Molecular Biology: A Laboratory Manual, Cold Spring Harbor Laboratories, Cold Spring Harbor, N.Y., 1989.

The subject peptides may be prepared by synthesis or by using recombinant techniques, as indicated above. Various commercial synthetic apparatuses are available, for example automated synthesizers by Applied Biosystems Inc., Foster City, Calif., Beckman, etc. By using synthesizers, naturally occurring amino acids may be substituted with unnatural amino acids, particularly D-stereoisomers, side chains having different lengths or functionalities, and the like. For recombinant techniques, one may prepare a nucleic acid sequence which encodes a plurality of the subject peptides in tandem, with an intervening amino acid or sequence, which allows for cleavage to the single peptide or head to tail dimer. Where methionine is absent, one may have an intervening methionine which allows for single amino acid cleavage. Alternatively, one may introduce consensus sequences, which are recognized by particular proteases for enzymatic cleavage. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like. Of particular interest are peptides of at least 2, more usually 3 and not more than about 60 lysine groups, particularly polylysines of from about 4 to 20, usually 6 to 18 lysine units, referred to as MAP, where the subject peptides are bonded to the lysine amino groups, generally at least about 20%, more usually at least about 50%, of available amino groups, to provide a multipeptide product. Thus, one obtains molecules having a plurality of the subject peptides where the orientation of the subject peptides is in the same direction, in effect one has a linking group to provide for tail to tail di- or oligomerization. Alternatively, other naturally occurring or synthetic peptides and proteins may be used to provide a backbone for attachment of the subject peptides at the C terminus.

For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

For the most part, the peptides of the subject invention will employ the amino acids naturally found at the α1-domain, except as specifically indicated. While the combinations of amino acids may not be naturally found, the individual amino acid will usually be present in one or more α1 domains. However, as is well known, the contacts from a peptide do not involve all the amino acids, but only those amino acids which are involved with the conformation of the reciprocal binding member. Therefore, significant latitude is permitted with intervening amino acids, which are not involved with the contact points and are of a size and polar nature, so as not to significantly change the orientation of the amino acids involved in contacts. Thus, one may have up to and including 2 mutations, usually not more than about 1 mutation, whereby mutation is intended that one does not find that amino acid present at that particular site in the HLA-B α1-domain and the analogous other species, particularly mouse, excluding the tryptophan at amino acid 86 as coming within the number of mutations.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like. Alternatively, one may provide for a wide variety of labels, as described previously, including ligands for binding to antibodies or natural receptors, where the peptides may be bound to a support or, alternatively, to another molecule. As already indicated, subject peptides may bind to Hsc70, which allows for isolation and purification of Hsc70 from other proteins found in the cell.

The subject peptides may be used for modulating activation of CTL and/or NK cells. By combining the subject peptides with the lymphocytes, activation of the CTLs by antigen presenting cells is modulated, generally by at least about 20%, more usually at least 40%, and preferably at least about 60%, based on percent lysis as described in the experimental section. The $IC_{50}$ for lysis will generally be less than about 500 μl, generally less than about 200 μl, and more than about 0.1 μl, usually more than about 1 μl.

The subject compositions can be used in vitro to inhibit lysis by T cells of target antigen presenting cells. Thus, in research where one wishes to maintain mixtures of cells, where CTLs would be activated and kill antigen presenting cells, such as macrophages or B-lymphocytes, or other cells which might serve as target cells, e.g., neoplastic cells, viral infected cells, or the like, the lysis can be inhibited so that the cellular population may be maintained while under investigation.

The subject compositions may also be used ex vivo. In cases of transplantation of organs, particularly solid organs or particular cells, whether xenogeneic or allogeneic, the donor organ may be bathed in a medium comprising the subject peptides. In this way, CTLs present with the implant will be inhibited from participating in graft versus host disease. Also, during the period when the subject peptides remain bound to the implant, the recipient's CTLs will be inhibited from being activated. Generally, the concentration of the peptide will vary in the medium, depending upon the activity of the peptide, the level of inhibition desired, the presence of other compounds affecting CTL activation, and the like. Usually, the concentration will be in the range of about 0.1 to 100 μg/ml, more usually in the range of about 1 to 10 μg/ml. Other immunosuppressants which may be present include cyclosporin A, FK506, antibodies for plasma membrane proteins associated with graft rejection, such as antibodies to CD4, CD8, CD2, LFA-1, ICAM-1, CD28, and the like. Subtherapeutic dosages will be employed, generally when present, not less than about 5% of the normal dosage, and not more than about 75%, usually in the range of about 10 to 60%. Other components of the bathing medium will generally be constituents normally used in an organ preservation solution, e.g. HBSS. The time for the organ to be maintained in the medium will generally be in the range of about 2 to 72 h.

The subject compositions may be also employed in vivo, administrating the subject compositions by any convenient means. The subject compositions may be administered prior to implantation, administration usually beginning not later than about 14 days prior to implantation, there preferably being at least one dosage administered within three days of administration. The subject compositions may be administered in the period beginning about 6 h prior to implantation and may be continued on a predetermined schedule thereafter, usually not past 30 days, more usually not past 20 days. However, after implantation, the subject compositions may be administered as needed, depending upon the response of the recipient to the organ or cells. In some situations, the subject compositions may be administered chronically, as long as the implant is present in the host.

Generally, a bolus of the subject composition which is administered will be in the range of about 0.1–50, more usually from about 1–25 mg/kg, of host. The host may be any mammal including domestic animals, pets, laboratory animals, primates, particularly humans. The amount will generally be adjusted depending upon the half life of the peptide, where the half life will generally be at least one minute, more usually at least about 10 min, desirably in the range of about 10 min to 12 h. Short half-lives are acceptable, so long as efficacy can be achieved with individual dosages or continuous infusion or repetitive dosages. Dosages in the lower portion of the range and even lower dosages may be employed, where the peptide has an enhanced half life or is provided as a depot, such as a slow release composition comprising particles, introduced in a matrix which maintains the peptide over an extended period of time, e.g., a collagen matrix, use of a pump which continuously infuses the peptide over an extended period of time over a substantially continuous rate, or the like.

The transplantation may involve any organ or cells, including organs such as a heart, kidneys, lung, eyes, liver, gut, vascular vessel, or other organ, and cells, such as β-islet cells, bone marrow cells, or other cells, where the organ or cells are allogeneic or xenogeneic, particularly where one or more of the Class I or II MHC antigens are different in the donor as compared to the recipient.

The subject peptides, by themselves or as conjugates, may be prepared as formulations in pharmaceutically acceptable media, for example, saline, PBS, aqueous ethanol, glucose, propylene glycol, or the like or as solid formulations in appropriate excipients, generally at a pharmacologically effective dose. The concentrations of the peptides will be determined empirically in accordance with conventional procedures for the particular purpose. The formulations may include bactericidal agents, stabilizers, buffers, or the like. The amount administered to the host will vary depending upon what is being administered, the purpose of the administration, such as prophylaxis or therapy, the state of the host, the manner of administration, the number of administrations and the interval between administrations, and the like. In order to enhance the half life of the subject peptide or subject peptide conjugates, the peptides may be encapsulated, introduced into the lumen of liposomes, prepared as a colloid, or other conventional technique may be employed, which provides an extended life time of the peptides ex vivo or in vivo.

The following examples are offered by way of illustration and not by way of limitation.

The following peptides were prepared to demonstrate the efficacy of the subject compositions.

| | | |
|---|---|---|
| SEQ ID NO: 4<br>2 | | Bi S G S G R V N L R I A L R Y |
| SEQ ID NO: 5<br>3 | | Bi S G S G R E N L R T A L R Y |
| SEQ ID NO: 6<br>4 | Kk | Bi S G S G R V N L R T A L R Y |
| SEQ ID NO: 7<br>5 | | Bi S G S G R E D L R I A L R Y |
| SEQ ID NO: 8<br>6 | | Bi S G S G R E N L R I L L R Y |
| SEQ ID NO: 9<br>7 | Dk | Bi S G S G R V D L R T L L R Y |
| SEQ ID NO: 10<br>8 | | Bi S G S G R E S L R I A L R Y |
| SEQ ID NO: 11<br>9 | 2Kk | Bi S G S G R V S L R T A L R Y |
| SEQ ID NO: 12<br>10 | | Bi S G S G R E N I R N A L R Y |
| SEQ ID NO: 13<br>11 | | Bi S G S G R E N L R I A R R Y |
| SEQ ID NO: 14<br>12 | | Bi S G S G R E N L R I A L G Y |
| SEQ ID NO: 15<br>13 | Con | Bi S G S G R E S L R N L R G Y |
| SEQ ID NO: 16<br>14 | | Bi S G S G E N L R I A L R Y Y |
| SEQ ID NO: 17<br>15 | | Bi S G S G N L R I A L R Y Y W |
| SEQ ID NO: 18<br>16 | | Bi S G S G L R I A L R Y Y W D |
| SEQ ID NO: 19<br>17 | | Bi S G S G I A L R Y Y W D S |

-continued

| | | |
|---|---|---|
| SEQ ID NO: 20<br>18 | | Bi S G S G A L R Y Y W D S E |
| SEQ ID NO: 21<br>19 | | Bi S G S G L R Y Y W D S E A |
| SEQ ID NO: 22<br>20 | | Bi S G S G R I A L R A A A |
| SEQ ID NO: 23<br>21 | | Bi S G S G R I A L R A A A A |
| SEQ ID NO: 24<br>22 | | Bi S G S G E N L R I A L R Y |
| SEQ ID NO: 25<br>23 | | Bi S G S G N L R I A L R Y |
| SEQ ID NO: 26<br>24 | | Bi S G S G L R I A L R Y |
| SEQ ID NO: 27<br>25 | | Bi S G S G D R E N L R I A L R |
| SEQ ID NO: 28<br>26 | | Bi S G S G T D R E N L R I A L |
| SEQ ID NO: 29<br>27 | | Bi S G S G Q T D R E N L R I A |
| SEQ ID NO: 30<br>28 | | Bi S G S G A Q T D R E N L R I |
| SEQ ID NO: 31<br>29 | | Bi S G S G R E N L R I A L R |
| SEQ ID NO. 32<br>30 | | Bi S G S G R E N L R I A L |
| SEQ ID NO. 33<br>31 | | Bi S G S G R E N L R I A |
| SEQ ID NO: 34<br>32 | | Bi S G S G A E N L R I A L R Y |
| SEQ ID NO: 35<br>33 | | Bi S G S G R A N L R I A L R Y |
| SEQ ID NO: 36<br>34 | | Bi S G S G R E A L R I A L R Y |
| SEQ ID NO: 37<br>35 | | Bi S G S G R E N A R I A L R Y |
| SEQ ID NO: 38<br>36 | | Bi S G S G R E N L A I A L R Y |
| SEQ ID NO: 39<br>37 | | Bi S G S G R E N L R A A L R Y |
| SEQ ID NO: 40<br>38 | | Bi S G S G R E N L R I A A R Y |
| SEQ ID NO: 41<br>39 | | Bi S G S G R E N L R I A L A Y |
| SEQ ID NO: 42<br>40 | | Bi S G S G R E N L R I A L R A |
| SEQ ID NO: 43<br>41 | RTIAa | Bi S G S G R V D L R T L R G Y |
| SEQ ID NO: 44<br>42 | RTIAu | Bi S G S G R V S L R N L R G Y |
| SEQ ID NO: 45<br>43 | E | Bi S G S G R V N L R T L R R Y |
| SEQ ID NO. 46<br>44 | G | Bi S G S G R M N L Q T L R G Y |
| SEQ ID NO: 47<br>45 | Dd | Bi S G S G R V D L R T A L R Y |
| SEQ ID NO: 48<br>46 | Ld | Bi S G S G R V N L R T L L G Y |
| SEQ ID NO: 49<br>47 | Kd | Bi S G S G R V S L R T A Q R Y |
| Bue 1 | 2702<br>MAP | |
| SEQ ID NO: 50<br>Bue 2 | | E N L R I A L R Y |
| SEQ ID NO: 51<br>Bue 3 | | E N L R I A L R |
| SEQ ID NO: 52<br>Bue 4 | | E N L R I A L |
| SEQ ID NO: 53<br>Bue 5 | | N L R I A L |
| SEQ ID NO: 54<br>Woo 1 | | R V S L R T A L R Y |
| SEQ ID NO: 55<br>Woo 2 | Bio-2702 | Bi S G S G R E N L R I A L R Y |

Materials and Methods

Animals. Adult 6–8 week old male C57BL6/J (B6, H-$2^d$), Balb/c(H-$2^d$) and CBA/J (H-$2^k$) mice were purchased from the Jackson Laboratory, Bar Harbor, Me. They were kept and maintained in the animal facility in the Sangstat Medical Corporation according to NIH guidelines and regulations of the Department of Health.

Peptide Preparation. Peptides were synthesized at UCB Bioproducts (Belgium) using an automated peptide synthesizer and Fmoc chemistry. The peptides had the format biotin-SGSA-peptide-OH. The peptides were dissolved in DMSO (Sigma) and then aliquoted at 50 mg/ml. Peptides were then stored at −20° C. until analysis. Peptides were purified by preparative reverse phase HPLC and shown to be >98% homogenous by analytical reverse phase HPLC. Amino acid content was confirmed by amino acid analysis. Before use, peptides were first dissolved in 1 volume of DMSO (Sigma) followed by addition of 99 volume of culture medium. The final concentration of DMSO in culture was not greater than 0.25%.

Preparation of Cell Suspension. Spleen cell suspensions were prepared following lysis of red blood cells by hypotonic shock. Cells were then washed in culture medium and finally resuspended in RPMI-1640 with 10% FBS (R-10 medium) or in serum-free AIM-V medium (Gibco, Grand Island, N.Y.).

Anti-CD3 Stimulation and Mixed Lymphocyte Culture. Spleen cells isolated from CBA mice were stimulated ($2\times10^5$/well) with anti-CD3 monoclonal antibody (Pharmingen, San Diego) at a final concentration of 0.1 to 1 μg/ml in 96-well, round-bottom microculture plates (Nunc, Denmark). Peptides at various concentrations were added at the beginning of the culture. Cells were incubated for a period of 3 days at 37° C., 5% $CO_2$. Twenty-four hours before harvesting 1 μCi[$^3$H]-TdR (Amersham, Arlington Heights, Ill.) was added to individual wells. Cells were then harvested using a Filtermate 196 Harvester (Packard, Downers Grove, Ill.) and the degree of thymidine incorporation was measured using a TopCount Microplate Scintillation Counter (Packard). For MLR, CBA spleen cells were used as responders and B6 spleen cells as stimulators. B6 spleen cells were pre-treated with mitomycin-C (Calbiochem, La Jolla, Calif.) at 0.5 mg/ml for 20 min at 36° C. Cells were then washed three times to remove excess mitomycin-C. CBA spleen cells ($2\times10^5$/well) were cultured with an equal number of mitomycin C-treated B6 cells in serum-free Aim V medium for periods of 3 to 6 days. One microcurie of [$^3$H]-TdR was added to the culture 24 hour before cell harvesting and the degree of thymidine incorporation was quantified as described above.

Cytotoxic T Cell Activity. To assay the effect of peptides on cytotoxic T cell activity, CBA to B6 effector cells were prepared following a 6-day culture of $4\times10^6$ CBA spleen cells with $5\times10^6$ mitomycin-treated B6 spleen cells in wells of a 24 well plate (Nuncion Delta, Nunc, Denmark) in RPMI-1640 with 10% FBS. Effector cells were then harvested and washed. EL4 (H-$2^b$), a mouse lymphoma induced in C57BL/6N was used as target cells. Cultured EL4 cells were maintained and sub-cultured once every three days ($^{51}$Cr) in 20 μl for 1 hour at 37° C. Effector (E) and target (T) cells were then added into V-shaped tissue culture plates (Nunc, Denmark) at E:T ratios of 3:1, 10:1, 30:1, 100:1, respectively. Peptides were diluted to the working concentrations with R-10 medium and added at the beginning of the 4-hour incubation period. For the determination of maximal release, 1% Triton X-100 was added to separate wells. Plates were then centrifuged for 2 min to increase cellular contact before the 4-hour incubation period. After incubation, 75 μl supernatant from each well was collected and the amount of $^{51}$Cr was counted using a TopCount Scintillation Counter. The degree of cell lysis was calculated using the formula below:

$$\%\ \text{Lysis} = \frac{CPM_{Experimental} - CPM_{Spontaneous}}{CPM_{Total} - CPM_{Spontaneous}}$$

NK Cell Activity. YAC-1, a mouse lymphoma which was induced by inoculation of Moloney leukemia virus into a newborn A/Sn mouse was used as the NK cell target (ATCC TIB 160). Four thousand sodium chromate labeled YAC-1 cells were cultured with different concentrations of freshly isolated CBA spleen cells (effector to target ratios: 62.5:1, 125:1, 250:1, 500:1) in V-shaped bottom plates with RPMI-1640 containing 10% FBS for 4 h at 37° C., 5% $CO_2$. The degree of cell lysis was quantified by the release of $^{51}$Cr into the supernatants. After incubation, plates were centrifuged and 75 μl of supernatant was collected. The degree of cell lysis was measured using a TopCount Scintillation Counter. The degree of cell lysis was calculated using the formula below:

$$\%\ \text{Lysis} = \frac{CPM_{Experimental} - CPM_{Spontaneous}}{CPM_{Total} - CPM_{Spontaneous}}$$

Activation Antigens Expression in Culture. Cells were cultured with 1 μg/ml anti-CD3 monoclonal antibody for 24 hour. Peptides were added at the beginning of the culture to a final concentration of 200 μg/ml. After incubation, cells were collected, washed and suspended in cold Hank's Balanced Salt Solution (HBSS) with 1% bovine serum albumin. Cells were then stained with the following biotinylated antibodies: anti-CD25 (IL-2 receptor α-chain, 1/400 dilution), anti-CD54 (ICAM-1, 1/200 dilution, anti-CD44 (Pgp-1, 1/200 dilution), and anti-CD69 (Very Early Activation Antigen, 1/200). Isotypic antibodies were used as negative controls. All antibodies were purchased from Pharmingen, San Diego. Fluorescein conjugated streptavidin was then added at 1/400 dilution. Stained samples were then analyzed using a FACScan flow cytometer (Becton Dickinson, San Jose, Calif.). Ten thousand events were acquired for each sample.

The results of the mixed lymphocyte culture were that peptides 2 and 15 inhibited CTL activity. The percentage lysis was reduced from 42% to 7% by the presence of peptide 15. In the same experiment, B2702 dimer partially inhibited the CTL activity, reducing it from 42% to 22%. Peptide 15 with the natural sequence covering the positions 77–85 terminating with tryptophan possesses the highest degree of inhibition. Peptides with position shifting to both ends of peptide 15 resulted in some reduction in the inhibitory activity. Other peptides showing inhibitory activity substantially greater than contol are peptides 4, 6, 16, 19, 20, 23, 27, and 34.

In a dose response study, of peptide B2702 monomer, the D-analog of B2702 MAP, peptide 15, and peptide 15-MAP, the B2702 monomer was found to inhibit the CTL activity in a dose-dependent manner. However, despite addition at high concentration, B2702 monomer was not able to inhibit the CTL response completely and 10% of CTL activity remained at 1 mg/ml. Peptide E, which was prepared in the same manner as peptide B2702 monomer and used in the same concentrations had no effect on CTL activity. Non-biotinylated peptide 15 inhibited the CTL, with $ED_{50}$ at 130

μg/ml. The polylysine (8 lysines) conjugate of peptide 15 had an enhanced potency, with a $ED_{50}$ at 25 μg/ml. The B2072-MAP (D-amino acid analog) had an $ED_{50}$ of 90 μg/ml.

To ascertain the effectiveness of peptide 15 on different MHC combinations, different mouse strain combinations were used including $H2^k>H2^b$, $H2^d>H2^b$ (change of effector type) and $H2^k>H2^d$ (change of target type). Peptide 15 was found to have greater activity than B2702 monomer across the 3 strain combinations employed. The increase in potency of peptide 15 MAP was also observed in the 3 strain combinations employed. These results demonstrate that peptide 15 is non-MHC restricted.

In the assay determining activity against NK cell activity, peptide 15 was able to inhibit the killing of YAC-1 (NK cell sensitive) cells by freshly isolated CBA spleen cells. The $ED_{50}$ of the inhibition is about 40 μg/ml. B2702 dimer had an $ED_{50}$ of about 100 μg/ml.

The effect of the peptides was then investigated as to their effect on stimulation by anti-CD3 antibodies. The B2702 monomer was found not to inhibit the anti-CD3 stimulation. The B2702 dimer showed inhibition of anti-CD3 stimulation. Peptides 2, 3, 15, 16, 17, 40, 41, 42, 43, Woo-2, Bue-1, -3, -4 and -5 were all shown to inhibit the anti-CD3 stimulation in a dose dependent manner, substantially complete inhibition being observed at 50 μg/ml, while substantially less inhibition is observed at 5 μg/ml, peptides 27, 42, 43 and Bue-5 showing significant levels of inhibition.

In the next study, human peripheral blood lymphocytes were isolated and stained with the biotinylated peptide panel. At 50 μg/ml, only peptide 2 and peptide 15 bound to the PBLs. Analysis of the binding of these two peptides revealed that the majority of the binding was on the macrophage/polymorphonuclear leukocytes population, with little or no binding on resting lymphocytes. Using human and murine cell lines, a spectrum of binding affinity was observed. Human Jurkat cell line E6-1 showed the highest degree of binding by peptide 15. The binding of peptide 15 to the Jurkat cell line suggests that the peptide 15 ligand may not be expressed in resting lymphocytes, but its expression is induced following lymphocyte activation. This finds further support in the observation that the binding of peptide 15 was observed in the anti-$H2^b$ CTL effector population (cells were activated as demonstrated by the expression of IL-2 receptor). In addition, the appearance of a distinct population bound by peptide 15 in the alloreactive T cells and PE815 cells suggests the presence of a putative receptor among the cell population.

To further demonstrate that the subject peptides bind to the same ligand, various peptides known to inhibit CTL activity were pre-incubated with the Jurkat cell line for 1 h, before the addition of the biotinylated peptide 15. The 2 MAP peptides (B2702 D-isomer) p15 MAP B2702 dimer and 2702 MAP (D-isomer) were employed. The 2 MAP peptides were able to block the binding of peptide 15, while the less effective peptides including peptide B2702 (D-amino acid) and dimer were not able to block the binding.

The in vivo immunosuppressive activity of the peptides was evaluated in heterotopic heart transplantation in the model described by Ono and Lindsey, (J Thorac Cardiovasc Surg 1969, 7:225). CBA recipients of B6 hearts were treated 10 mg/kg/day of p15 from day 0 to day 10 after transplantation. Untreated recipients rejected the allografts between day 6 and 10 (MST=7.5+/−1.1 days). Treatment of recipients with p15 lead to a significant increase of graft survival (MST=14.4+/−1.5 days, p vs control=0.0007; Mann-Whitney Test).

It is evident from the above results, that the subject compositions and methodologies provide for substantial inhibition of cytotoxicity of both CTLs and natural killer cells. Surprisingly, peptides comprising the triad YYW, where W substantially differs from the conserved naturally occurring amino acid of the HLA-B $\alpha_1$ domain provide for substantially increased effectiveness in inhibiting lysis as compared to earlier oligopeptides derived from the same region, but based on the naturally occurring sequence. The use of the subject compositions provides for substantial advantages in requiring lower amounts of the oligopeptide for therapeutic levels, and in an in vitro test, providing for substantially complete inhibition, in contrast to only substantial reduction with the prior compounds.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of inhibiting activation of cytotoxic T lymphocytes and/or natural killer cells, said method comprising:

combining said cells with an activation inhibiting amount of a compound comprising an oligopeptide of at least 6 amino acids comprising a contiguous sequence of a HLA-B $\alpha_1$ domain including amino acids 84–86, wherein amino acids 84 to 86 are YYW, Sequence ID NO: 1;

whereby activation of said cells is inhibited.

2. A method according to claim 1, wherein said oligopeptide is of at least 8 amino acids including amino acids 83 to 86, wherein amino acids 83 to 86 are RYYW, Sequence ID NO: 2.

3. A method according to claim 2 wherein said oligopeptide comprises at least a total of 6 contiguous amino acids from said HLA-B $\alpha_1$ domain joined to said RYYW, Sequence ID NO: 2.

4. A method according to claim 1, wherein said compound is a dimer of said oligopeptide.

5. A method according to claim 1, wherein at least one of said amino acids is a D-stereoisomer.

6. A method according to claim 1, wherein said combining is in the presence of a viable solid organ or viable second cells other than cytotoxic T lymphocytes and/or natural killer cells.

7. A method of inhibiting activation of cytotoxic T lymphocytes and/or natural killer cells, said method comprising:

combining said cells with an activation inhibiting amount of a compound comprising an oligopeptide of at least 6 amino acids, including a triad YYW, Sequence ID NO: 1, and comprising a contiguous sequence of the sequence:

$aa^{70}$ $aa^{71}$ Q $aa^{73}$ $aa^{74}$ R $aa^{76}$ $aa^{77}$ L $aa^{79}$ $aa^{80}$ $aa^{81}$ $aa^{82}$ $aa^{83}$ Y Y W $aa^{87}$ $aa^{88}$ $aa^{89}$ $aa^{90}$ $aa^{91}$ (SEQ ID NO:56)

wherein:

$aa^{70}$ is Q, H, S, N or K;

$aa^{71}$ is an aliphatic neutral amino acid;

$aa^{73}$ is T or A;

$aa^{74}$ is Y or H;

$aa^{76}$ is aliphatic neutral amino acid;

$aa^{77}$ is S or N;

$aa^{79}$ is R or G;

$aa^{80}$ is T, I, N or an aromatic amino acid;

$aa^{81}$ is an aliphatic non-polar amino acid;

$aa^{82}$ is R, L or an aromatic amino acid;

$aa^{83}$ is G or R;

$aa^{87}$ is any amino acid;

$aa^{88}$ is an aromatic amino acid or aliphatic amino acid of from 5 to 6 carbon atoms;

$aa^{89}$ is any amino acid;

$aa^{90}$ is any amino acid; and $aa^{91}$ is any amino acid;

whereby activation of said cells is inhibited.

8. A method according to claim 7, wherein said oligopeptide is of at least 8 amino acids, is the dimer thereof, or at least one of the amino acids is the D-stereoisomer and is of the formula:

R V N L R I A/L L R Y Y W Q/D S (SEQ ID NO: 3)

wherein the backslashes intend that either amino acid may be present at that position.

9. A method according to claim 7, wherein said combining is in the presence of a viable solid organ or cells other than cytotoxic T lymphocytes and/or natural killer cells.

10. In a method for transplanting a donor mammalian organ or cells other than as part of a viable organ to a mammalian recipient, which method comprises:

isolating said donor organ or cells from said donor and implanting said donor organ or cells in said recipient, the improvement which comprises at least one of the following steps:

(a) combining said organ or cells prior to implanting in said mammalian recipient with an activation inhibiting amount of a compound comprising an oligopeptide of at least 6 amino acids comprising a contiguous sequence of a HLA-B $\alpha_1$ domain including amino acids 84 to 86, wherein amino acids 84 to 86 are YYW, Sequence ID NO: 1; or (b) administering to said mammalian recipient in a period extending from prior to subsequent to implanting said donor organ or cells an activation inhibiting amount of a compound comprising an oligopeptide of at least 6 amino acids comprising a contiguous sequence of a HLA-B $\alpha_1$ domain including amino acids 84 to 86, wherein amino acids 84 to 86 are YYW, Sequence ID NO: 1.

11. A method according to claim 10, wherein said compound is of the formula:

R V N L R I A/L L R Y Y W Q/D S (SEQ ID NO: 3)

wherein the backslashes intend that either amino acid may be present at that position.

12. A method according to claim 11, wherein said compound is a peptide of not more than 20 amino acids and comprises the amino acid sequence N L R I A L R Y Y W SEQ ID NO: 57.

* * * * *

SEQUENCE LISTING

```
<160> NUMBER OF SEQ ID NOS: 57

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic

<400> SEQUENCE: 1

Tyr Tyr Trp
  1


<210> SEQ ID NO 2
<211> LENGTH: 4
```

-continued

<212> TYPE: PRT
<213> ORGANISM: Artificial Sequence
<220> FEATURE:
<223> OTHER INFORMATION: Description of Artificial Sequence: Synthetic

<400> SEQUENCE: 2

Arg Tyr Tyr Trp
1

<210> SEQ ID NO 3
<211> LENGTH: 14
<212> TYPE: PRT
<213> ORGANISM: Artificial Sequence
<220> FEATURE:
<221> NAME/KEY: UNSURE
<222> LOCATION: (2)
<223> OTHER INFORMATION: The amino acid at position 2 can be either Valine or Glutamic acid.
<220> FEATURE:
<221> NAME/KEY: UNSURE
<222> LOCATION: (3)
<223> OTHER INFORMATION: The amino acid at position 3 can be either Asparagine or Aspartic acid.
<220> FEATURE:
<221> NAME/KEY: UNSURE
<222> LOCATION: (7)
<223> OTHER INFORMATION: The amino acid at position 7 can be either Alanine or Leucine.
<220> FEATURE:
<221> NAME/KEY: UNSURE
<222> LOCATION: (9)
<223> OTHER INFORMATION: The amino acid at position 9 can be either Arginine or Glutamic acid.
<220> FEATURE:
<221> NAME/KEY: UNSURE
<222> LOCATION: (13)
<223> OTHER INFORMATION: The amino acid at position 13 can be either Glutamine or Aspartic acid.
<220> FEATURE:
<223> OTHER INFORMATION: Description of Artificial Sequence: Synthetic

<400> SEQUENCE: 3

Arg Xaa Xaa Leu Arg Ile Xaa Leu Xaa Tyr Tyr Trp Xaa Ser
1 5 10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 4

Ser Gly Ser Gly Arg Val Asn Leu Arg Ile Ala Leu Arg Tyr
1 5 10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 5

Ser Gly Ser Gly Arg Glu Asn Leu Arg Thr Ala Leu Arg Tyr
1 5 10

<210> SEQ ID NO 6
<211> LENGTH: 14
<212> TYPE: PRT
<213> ORGANISM: Artificial Sequence -continued
<220> FEATURE:
<223> OTHER INFORMATION: Description of Artificial Sequence: Synthetic

<400> SEQUENCE: 6

Ser Gly Ser Gly Arg Val Asn Leu Arg Thr Ala Leu Arg Tyr
1 5 10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 7

Ser Gly Ser Gly Arg Glu Asp Leu Arg Ile Ala Leu Arg Tyr
1 5 10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 8

Ser Gly Ser Gly Arg Glu Asx Lys Arg Ile Leu Leu Arg Tyr
1 5 10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 9

Ser Gly Ser Gly Arg Val Asp Leu Arg Thr Leu Leu Arg Tyr
1 5 10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 10

Ser Gly Ser Gly Arg Glu Ser Leu Arg Ile Ala Leu Arg Tyr
1 5 10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 11

Ser Gly Ser Gly Arg Val Ser Leu Arg Thr Ala Leu Arg Tyr
1 5 10

<210> SEQ ID NO 12
<211> LENGTH: 14
<212> TYPE: PRT
<213> ORGANISM: Artificial Sequence
<220> FEATURE:

-continued

<223> OTHER INFORMATION: Description of Artificial Sequence: Synthetic

<400> SEQUENCE: 12

```
Ser Gly Ser Gly Arg Glu Asn Ile Arg Asn Ala Leu Arg Tyr
  1               5                  10
```

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 13

```
Ser Gly Ser Gly Arg Glu Asn Leu Arg Ile Ala Arg Arg Tyr
  1               5                  10
```

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 14

```
Ser Gly Ser Gly Arg Glu Asn Leu Arg Ile Ala Leu Gly Tyr
  1               5                  10
```

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 15

```
Ser Gly Ser Gly Arg Glu Ser Leu Arg Asn Leu Arg Gly Tyr
  1               5                  10
```

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 16

```
Ser Gly Ser Gly Glu Asn Leu Arg Ile Ala Leu Arg Tyr Tyr
  1               5                  10
```

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 17

```
Ser Gly Ser Gly Asn Leu Arg Ile Ala Leu Arg Tyr Tyr Trp
  1               5                  10
```

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic -continued

<400> SEQUENCE: 18

Ser Gly Ser Gly Leu Arg Ile Ala Leu Arg Tyr Tyr Trp Asp
1 5 10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 19

Ser Gly Ser Gly Ile Ala Leu Arg Tyr Tyr Trp Asp Ser
1 5 10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 20

Ser Gly Ser Gly Ala Leu Arg Tyr Tyr Trp Asp Ser Glu
1 5 10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 21

Ser Gly Ser Gly Leu Arg Tyr Tyr Trp Asp Ser Glu Ala
1 5 10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 22

Ser Gly Ser Gly Arg Ile Ala Leu Arg Ala Ala Ala
1 5 10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 23

Ser Gly Ser Gly Arg Ile Ala Leu Arg Ala Ala Ala Ala
1 5 10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic -continued

<400> SEQUENCE: 24

```
Ser Gly Ser Gly Glu Asn Leu Arg Ile Ala Leu Arg Tyr
  1               5                  10
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 25

```
Ser Gly Ser Gly Asn Leu Arg Ile Ala Leu Arg Tyr
  1               5                  10
```

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic

<400> SEQUENCE: 26

```
Ser Gly Ser Gly Leu Arg Ile Ala Leu Arg Tyr
  1               5                  10
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 27

```
Ser Gly Ser Gly Asp Arg Glu Asn Leu Arg Ile Ala Leu Arg
  1               5                  10
```

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 28

```
Ser Gly Ser Gly Thr Asp Arg Glu Asn Leu Arg Ile Ala Leu
  1               5                  10
```

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 29

```
Ser Gly Ser Gly Gln Thr Asp Arg Glu Asn Leu Arg Ile Ala
  1               5                  10
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 30

-continued

```
Ser Gly Ser Gly Ala Gln Thr Asp Arg Glu Asn Leu Arg Ile
  1               5                  10


<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic

<400> SEQUENCE: 31

Ser Gly Ser Gly Arg Glu Asn Leu Arg Ile Ala Leu Arg
  1               5                  10


<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 32

Ser Gly Ser Gly Arg Glu Asn Leu Arg Ile Ala Leu
  1               5                  10


<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic

<400> SEQUENCE: 33

Ser Gly Ser Gly Arg Glu Asn Leu Arg Ile Ala
  1               5                  10


<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 34

Ser Gly Ser Gly Ala Glu Asn Leu Arg Ile Ala Leu Arg Tyr
  1               5                  10


<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 35

Ser Gly Ser Gly Arg Ala Asn Leu Arg Ile Ala Leu Arg Tyr
  1               5                  10


<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 36
```

-continued

Ser Gly Ser Gly Arg Glu Ala Leu Arg Ile Ala Leu Arg Tyr
1 5 10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 37

Ser Gly Ser Gly Arg Glu Asn Ala Arg Ile Ala Leu Arg Tyr
1 5 10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 38

Ser Gly Ser Gly Arg Glu Asn Leu Ala Ile Ala Leu Arg Tyr
1 5 10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 39

Ser Gly Ser Gly Arg Glu Asn Leu Arg Ala Ala Leu Arg Tyr
1 5 10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 40

Ser Gly Ser Gly Arg Glu Asn Leu Arg Ile Ala Ala Arg Tyr
1 5 10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 41

Ser Gly Ser Gly Arg Glu Asn Leu Arg Ile Ala Leu Ala Tyr
1 5 10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 42

Ser Gly Ser Gly Arg Glu Asn Leu Arg Ile Ala Leu Arg Ala

-continued

```
  1               5                   10


<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 43

Ser Gly Ser Gly Arg Val Asp Leu Arg Thr Leu Arg Gly Tyr
  1               5                   10


<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 44

Ser Gly Ser Gly Arg Val Ser Leu Arg Asn Leu Arg Gly Tyr
  1               5                   10


<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 45

Ser Gly Ser Gly Arg Val Asn Leu Arg Thr Leu Arg Arg Tyr
  1               5                   10


<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 46

Ser Gly Ser Gly Arg Met Asn Leu Gln Thr Leu Arg Gly Tyr
  1               5                   10


<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 47

Ser Gly Ser Gly Arg Val Asp Leu Arg Thr Ala Leu Arg Tyr
  1               5                   10


<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 48

Ser Gly Ser Gly Arg Val Asn Leu Arg Thr Leu Leu Gly Tyr
  1               5                   10
```

-continued

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 49

Ser Gly Ser Gly Arg Val Ser Leu Arg Thr Ala Gln Arg Tyr
1 5 10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 50

Glu Asn Leu Arg Ile Ala Leu Arg Tyr
1 5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic

<400> SEQUENCE: 51

Glu Asn Leu Arg Ile Ala Leu Arg
1 5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 52

Glu Asn Leu Arg Ile Ala Leu
1 5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 53

Asn Leu Arg Ile Ala Leu
1 5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 54

Arg Val Ser Leu Arg Thr Ala Leu Arg Tyr
1 5 10

-continued

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 55

```
Ser Gly Ser Gly Arg Glu Asn Leu Arg Ile Ala Leu Arg Tyr
  1               5                  10
```

<210> SEQ ID NO 56
<211> LENGTH: 22
<212> TYPE: PRT
<213> ORGANISM: Artificial Sequence
<220> FEATURE:
<221> NAME/KEY: UNSURE
<222> LOCATION: (1)
<223> OTHER INFORMATION: The amino acid at position 1 can be either Glutamine, Histidine, Serine, Asparagine or Lysine.
<220> FEATURE:
<221> NAME/KEY: UNSURE
<222> LOCATION: (2)
<223> OTHER INFORMATION: The amino acid at position 2 is an aliphatic neutral amino acid, including Serine, Alanine and Threonine.
<220> FEATURE:
<221> NAME/KEY: UNSURE
<222> LOCATION: (4)
<223> OTHER INFORMATION: The amino acid at position 4 can be either Threonine or Alanine.
<220> FEATURE:
<221> NAME/KEY: UNSURE
<222> LOCATION: (5)
<223> OTHER INFORMATION: The amino acid at position 5 can be either Tyrosine or Histidine.
<220> FEATURE:
<221> NAME/KEY: UNSURE
<222> LOCATION: (7)
<223> OTHER INFORMATION: The amino acid at position 7 is an aliphatic neutral amino acid, particularly Valine.
<220> FEATURE:
<221> NAME/KEY: UNSURE
<222> LOCATION: (8)
<223> OTHER INFORMATION: The amino acid at position 8 can be either Serine or Asparagine.
<220> FEATURE:
<221> NAME/KEY: UNSURE
<222> LOCATION: (10)
<223> OTHER INFORMATION: The amino acid at position 10 can be either Arginine or Glycine.
<220> FEATURE:
<221> NAME/KEY: UNSURE
<222> LOCATION: (11)
<223> OTHER INFORMATION: The amino acid at position 11 can be either Threonine, Isoleucine, Aspargine or an aromatic amino acid such as Phenyalanine, Tryptophan or Tyrosine.
<220> FEATURE:
<221> NAME/KEY: UNSURE
<222> LOCATION: (12)
<223> OTHER INFORMATION: The amino acid at position 12 is an aliphatic non-polar amino acid including Leucine or Alanine.
<220> FEATURE:
<221> NAME/KEY: UNSURE
<222> LOCATION: (13)
<223> OTHER INFORMATION: The amino acid at position 13 is either Arginine, Leucine or aromatic amino acid.
<220> FEATURE:
<221> NAME/KEY: UNSURE
<222> LOCATION: (14)
<223> OTHER INFORMATION: The amino acid at position 14 can be either Glycine or Arginine.
<220> FEATURE:
<221> NAME/KEY: UNSURE -continued

```
<222> LOCATION: (18)
<223> OTHER INFORMATION: The amino acid at position 18 is any amino
      acid, particularly neutral aliphatic or aromatic,
      Glycine, Alanine, Serine, Threonine, Methionine,
      Asparagine, Glutamine, Phenyalanine, Tryptophan,
      Tyrosine.
<220> FEATURE:
<221> NAME/KEY: UNSURE
<222> LOCATION: (19)
<223> OTHER INFORMATION: The amino acid at position 19 is an aromatic
      amino acid or aliphatic amino acid from 5 to 6 carbon
      atoms, particularly Phenyalanine, Tryptophan,
      Tyrosine, Leucine, Isoleucine or Valine.
<220> FEATURE:
<221> NAME/KEY: UNSURE
<222> LOCATION: (20)
<223> OTHER INFORMATION: The amino acid at position 20 is any amino
      acid, particulary neutral aliphatic or aromatic,
      Glycine, Alanine, Serine, Threonine, Methionine,
      Asparagine, Glutamine, Phenyalanine, Tryptophan,
      Tyrosine.
<220> FEATURE:
<221> NAME/KEY: UNSURE
<222> LOCATION: (21)
<223> OTHER INFORMATION: The amino acid at position 21 is any amino
      acid, particularly neutral aliphatic or aromatic,
      Glycine, Alanine, Serine, Threonine, Methionine,
      Asparagine, Glutamine, Phenyalanine, Tryptophan,
      Tyrosine.
<220> FEATURE:
<221> NAME/KEY: UNSURE
<222> LOCATION: (22)
<223> OTHER INFORMATION: The amino acid at position 22 is any amino
      acid, particulary neutral aliphatic or aromatic,
      Glycine, Alanine, Serine, Threonine, Methionine,
      Asparagine, Glutamine, Phenyalanine, Tryptophan,
      Tyrosine.
<220> FEATURE:
<223> OTHER INFORMATION: Description of Artificial Sequence: Synthetic

<400> SEQUENCE: 56

Xaa Xaa Gln Xaa Xaa Arg Xaa Xaa Leu Xaa Xaa Xaa Xaa Xaa Tyr Tyr
  1               5                  10                  15

Trp Xaa Xaa Xaa Xaa Xaa
             20


<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic

<400> SEQUENCE: 57

Asn Leu Arg Ile Ala Leu Arg Tyr Tyr Trp
  1               5                  10
```